United States Patent [19]

Ohishi

[11] 4,027,982
[45] June 7, 1977

[54] NEEDLE DETECTOR FOR CIRCULAR KNITTING MACHINES

[75] Inventor: Tadashi Ohishi, Osaka, Japan

[73] Assignee: Kyodo Denshi Kogyo Co., Ltd., Osaka, Japan

[22] Filed: Apr. 23, 1975

[21] Appl. No.: 570,789

[52] U.S. Cl. .............................. 356/237; 66/157; 66/165; 250/224; 250/227; 250/561

[51] Int. Cl.² .............. G01N 21/16; G01N 21/30; D04B 35/10

[58] Field of Search ........... 356/237; 250/561, 563, 250/572, 227, 224; 66/165, 157

[56] References Cited
UNITED STATES PATENTS

| | | | |
|---|---|---|---|
| 3,459,240 | 8/1969 | Erickson | 250/227 |
| 3,529,445 | 9/1970 | Brose | 66/165 |
| 3,566,083 | 2/1971 | McMillin | 250/227 |
| 3,771,325 | 11/1973 | Sweeney et al. | 66/157 |
| 3,796,500 | 3/1974 | Obser | 356/237 |
| 3,885,879 | 5/1975 | Louder et al. | 250/227 |
| 3,904,529 | 9/1975 | Nakamura | 250/227 |
| 3,937,038 | 2/1976 | Sick | 356/237 |

Primary Examiner—Vincent P. McGraw
Attorney, Agent, or Firm—Nathan Levin

[57] ABSTRACT

Improvement in apparatus used for the continuous inspection of the moving circle of needles of a circular knitting machine to detect faulty needles which comprises a first group of optical glass fibers to guide light from a light source to the needles and a second group of optical fibers to guide reflected light from the needles to a photoelectric sensing member, the end portions of said groups of optical glass fibers at the needles being intermingled to form a single bundle of such intermingled fibers.

3 Claims, 8 Drawing Figures

U.S. Patent  June 7, 1977  4,027,982
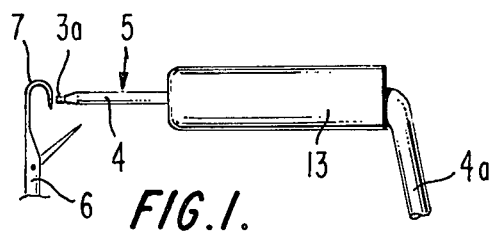
FIG.1.
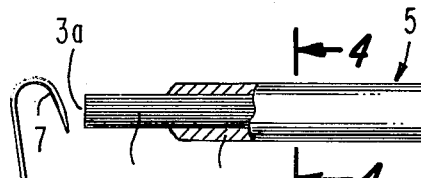
FIG.2.
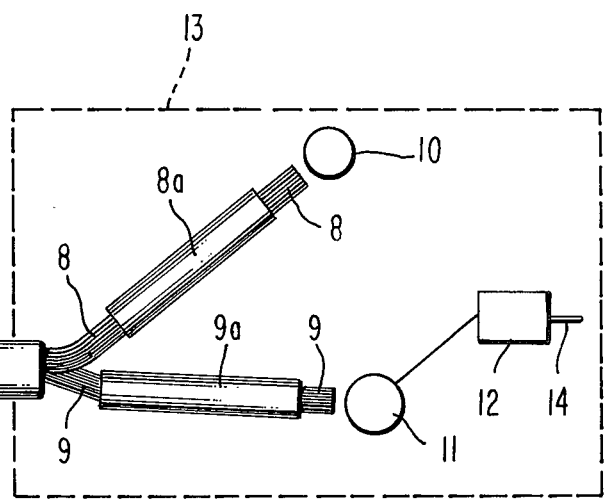
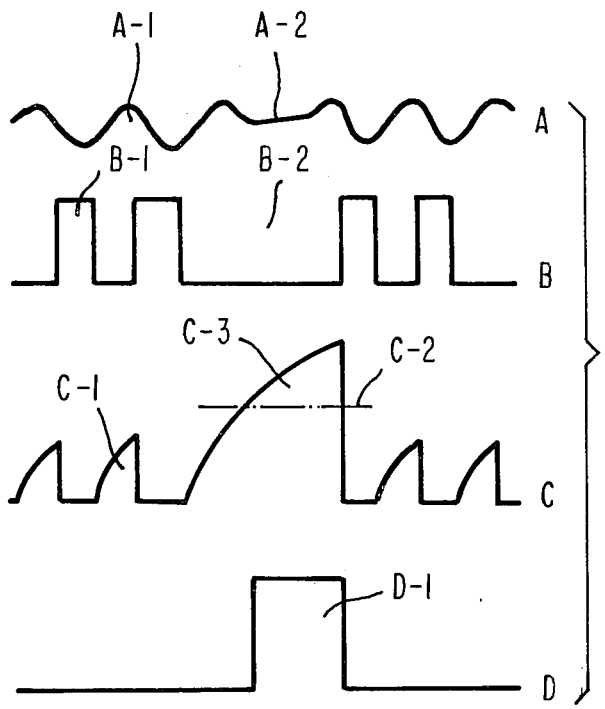
FIG.8.
FIG.3.
FIG.5.
FIG.6.
FIG.4.
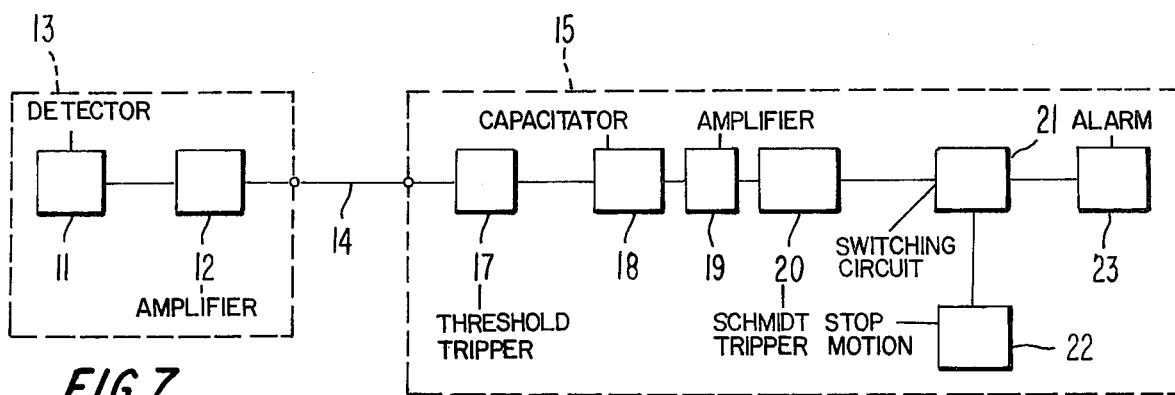
FIG.7.

NEEDLE DETECTOR FOR CIRCULAR KNITTING MACHINES

The present invention relates generally to the art of knitting and more particularly to apparatus used with circular knitting machines for the continuous inspection of its circle of latch needles to detect faulty ones thereof when the machine is in operation. The apparatus acts to stop the machine and/or provide an audable or visual alarm when a faulty needle is detected.

In inspection apparatus of this type is known in the knitting art, an example thereof is disclosed in United States Patent to Peter Brose, inventor, issued Sept. 22, 1970. In such apparatus, light from a suitable source is guided to and is impinged upon consecutive ones of the moving circle of needles of a circular knitting machine and light reflected back from said needles is guided to and is impinged upon a photoelectric sensing member, the light being guided to and away from said needles by optical lens systems. The sensing member, in response to the needle images formed by the reflected light impinge thereon, emits signals which reflect the condition of the needles, that is, if there are no faulty needles, the needle produced signals will be of normal and uniform character, whereas, if there are faulty needles, the corresponding needle produced signals, in response thereto, will be of abnormal and non-uniform character. Such normal and abnormal needle produced signals are fed into an electronic evaluating circuit which, in response to the abnormal signals, acts to stop the machine and/or to produce an audable or visual alarm. In one form of such evaluating circuit, each of such needle produced signals acts in turn to discharge a constantly charged capacitor so that the latter produces saw tooth signals of uniform amplitude when the needle produced signals are normal, and produces saw tooth signals of abnormal amplitude when the needle produced signals are abnormal. The saw tooth signals are then fed into an electronic tripper having a suitable threshold value so that only in response to a saw tooth signal of abnormal amplitude does the tripper emit its own signal. Such tripper signal is then used, via suitable switching means, to stop the machine and/or to provide an audable or visual alarm.

It is the object of the present invention to provide an improvement in the light guiding means used in the above described type of apparatus, such improvement comprising the use of specially arranged groups of individual optical glass fibers to guide light to and away from the needles. Such fibers are flexable in character and are preferably arranged in parallel relation within the said groups thereof.

A first group of fibers extends between the needles and the light source and a second group of fibers extends between the needles and the photoelectric sensing member. The end portions of the two groups of fibers extending from the needles are intermingled and are formed into an individual composite bundle of such intermingled fibers, while the other end portions of the two groups of fibers are each formed into an individual bundle thereof. Accordingly, light is guided from its source to the needles by the first group of fibers and the light reflected back from the needles is guided to the photoelectric member by the second group of fibers.

With the above and other objects in view which will become apparent from the following detailed description of a preferred embodiment of the invention shown in accompanying drawings, the present invention resides in the novel elements of construction and arrangement of parts of the electronic inspection apparatus for the detection of faulty needles in circular knitting machines as illustrated and as hereinafter particularly pointed out in the appended claims. In the drawings:

FIG. 1 is a side elevational view of the inspection apparatus of the present invention as shown in operative relation to the hook of a latch needle, the apparatus having a protective cover for the two groups of optical glass fibers disposed therein, FIG. 2 is an enlarged view of the apparatus shown in FIG. 1 with portions of the cover broken away and shown in phantom lines in order to illustrate the disposition of the two groups of optical glass fibers in relation to each other and to the needle hook, to a light source and to a photoelectric sensing member, FIG. 3 is an elarged schematic view showing the needle hook in operative relation to the ends of a bundle of the two groups of intermingled fibers and showing how the light is guided from the light source to the needle hook by one group of fibers and how reflected light is guided away from the needle hook by the other group of fibers to the photoelectric sensing member.

FIG. 4 is a cross-sectional view taken on line 4—4 of FIG. 2 showing the bundle of intermingled fibers of the two groups thereof inside a cylindrical portion of the cover, FIG. 5 is a view of the upper portion of a latch needle with its hook broken away, FIG. 6 is a view of an enlarged needle hook, FIG. 7 is a block schematic diagram of the evaluating circuitry into which the needle produced signals are fed from the photoelectric sensing member receiving the same, and FIG. 8 is a schematic diagram showing the several wave patterns formed in the evaluating circuitry.

The inspection apparatus of the present invention for the detection of faulty needles in a circular knitting machine is shown in FIG. 1 in operative relation adjacent to hook 7 of a latch needle 6 of the machine, such needle being one of a circle of spaced similar needles present in the machine, the needles moving past the said apparatus when the machine is in operation. The apparatus shown in FIG. 1 comprises a relatively long and narrow housing 13, a hollow detection pin 5 secured to and extending from one end of the housing, the pin being formed of a slender cylindrical tube 4 having a tapered end from which extends a bundle of optical glass fibers the ends of which are indicated at 3a in close proximity to the needle hook. The apparatus of FIG. 1 may be secured to any desired stationary portion of the machine by suitable brackets (not shown), and it has a service cord 4a extending from the opposite end of the housing 13.

As shown in FIG. 2, a plurality of individual optical glass fibers are arranged in Y-shape with the V-shaped arms thereof each formed of similar groups 8 and 9 of a plurality of the glass fibers, and with the vertical leg of the Y-shape comprising a bundle of the fibers which are extensions of the fibers of both of the groups 8 and 9, such fiber extensions of the groups 8 and 9 thereof being intermingled in the bundle 3 of the fibers.

The bundle of fibers 3 is compactly disposed in tube 4 with its end 3a extending from the free end of the tube. The bundle of fibers 3 extends from tube 4 into housing 13 where it is divided into the two groups 8 and 9 of fibers. Group 8 fibers extend through and are compactly disposed in a tube 8a while group 9 fibers extend through and are compactly disposed in a tube 9 a, the tubes 8a and 9a being suitable secured to the inside of the housing 13. Each group 8 and 9 contains approximately half the number of fibers in the bundle 3 thereof, and the aforesaid intermingling of the fibers extending from the groups 8 and 9 into the bundle 3 is intended to provide a homogeneous mixture of the fibers from both groups thereof.

The group of fibers 8 terminates adjacent to a suitable light source 10 and the group of fibers 9 terminates adjacent a suitable photoelectric sensing member 11, so that light from source 10 is guided, via fiber group 8 and its extension in bundle 3, out through ends 3a thereof to impinge upon needle hooks 7, and light reflected back from the needle hook is guided by the fiber extensions of group 9 in the bundle 3 and then by the group 9 fibers to impinge upon the photoelectric sensing member 11. The space between the ends 3a of the intermingled fibers and the needles is unobstructed.

The movement of the light relative to the needle hook is shown schematically in FIG. 3 where alternate lines, of which one is indicated at 1, have arrows thereon pointing toward the needle hook while the intervening lines, of which one is indicated at 2, have arrows thereon pointing away from the needle hook. The lines 1 are representative of the extensions of the fibers of group 8 in bundle 3 while the lines 2 are representative of the extensions of the fibers of group 9 which are also in bundle 3. Light is guided along fibers 1 to the needle hook and is reflected back therefrom to be guided by fibers 2 to the photoelectric sensing member 11.

In the evaluating cirucitry of FIG. 7, the sensing member 11 is connected to an amplifer 12, which may also be disposed in the housing 13, then the amplifier 12 is connected, via 14, in service card 4a to a Schmidt trigger device 17 inside a suitably positioned control box 15. The service cord 4a between housing 13 and control box 15 permits the latter to be situate remote from the housing in any convenient spaced relation thereto. The Schmidt trigger is connected to a constantly charged capacitor 18 which in turn is connected to an amplifier 19 which latter is connected to a threshold tripper 20, the latter being connected to an output operating switching circuit in block 21 with the latter connected to block 22 having means to stop the machine and also being connected to block 23 having means to give an alarm.

When there are no faulty needles, the light from source 10, via fibers 1, needle hook 7 and fibers 2 will provide a uniform pattern of needle hook images to be impinged upon the sensing member 11, and this will cause the latter to emit a uniform sine wave of signals which, when amplified by unit 12, will appear as at A-1 in wave A of FIG. 8. When there is a faulty needle, such as needle 6, FIG. 5, without its hook 7a shown in dotted lines or when there is a needle with its hook 7b enlarged, FIG. 6, the signal emitted by sensing member 11 will be distorted as shown at A-2 in the wave A. The uniform needle produced signals A-1 of wave A are converted into uniform block signals B-1 of wave B by the Schmidt trigger 17 while the distorted signal A-2 of wave A will not be converted into any signal in wave B, the absence of such signal being indicated at B-2 in the wave B. Then wave B is fed into capacitor 18 wherein the signals B-1 of uniform amplitude are changed to the saw tooth signals C-1 of wave C, the signals C-1 also being of uniform amplitude. Where there is no signal in wave B, as at B-2, there is a saw tooth signal C-3 of abnormal amplitude in wave C. The wave C, after passing through amplifier 19, is fed into a trigger 20 having a suitable threshold so that only those signals of wave C having an amplitude above a level C-2 (that is, signal C-3) will provide a signal D-1 in wave D. Thus, for each faulty needle a signal D-1 is emitted from tripper 20. The signal D-1 is fed into the output switching circuit of block 21 which then acts, via block 22 and 23, to stop the machine and to signal an alarm.

While the present invention has been described for use in detecting faulty needles of circular knitting machines, it will be understood that it is not so limited and may be similarly used in straight knitting machines, and, may also be used in apparatus to detect faulty objects of any type which are uniformly arranged in a moving series thereof. The present invention may also be used with ciruclar knitting machines of the type having a stationary needle cylinder in which event the apparatus will rotate with the cam ring of the machine.

I claim:

1. Apparatus of the type used upon cirular knitting machines for continuous inspection of individual ones of a series of uniformly spaced like needles of such machines to detect faulty ones of such needles, wherein said apparatus is provided with a housing in extension of one end of a tube of predetermined length, the other end of said tube being free, wherein a light source, a photoelectric sensing member and an amplifier operatively related to said sensing member are disposed within said housing, wherein a bundle of a plurality of individual glass fibers of predetermined length are encased within and extend lengthwise of said tube and extend into said housing, wherein said bundle of fibers are divided into a first and a second group thereof with said groups of fibers being spaced within said housing and being intermingled within said tube, wherein said light source is operatively related to the ends of said first group of fibers within said housing, wherein said photoelectric sensing member is operatively related to the ends of said second group of fibers within said housing, wherein said intermingled fibers within said tube terminate adjacent to said free end thereof, said series of needles being movable relative to the ends of said intermingled fibers, said first group of fibers guiding light from said light source to impinge upon each of said moving needles, a quantity of such impinged light being reflected back from each of said needles, said second group of fibers guiding said reflected light to impinge upon said photoelectric sensing member, wherein said housing is disposed so as to be readily adjustable to placesaid free ends of said intermingled fibers in desired location closely adjacent to said moving needles, wherein the space between said needles and said ends of said intermingled fiber is unobstructed. and wherein said apparatus is provided with means to evaluate said reflected light received by said photoelelctric sensing member, 2. Apparatus as in claim 1 wherein said evaluating means produces a pulse train comprising a series of uniformly spaced signals corresponding to the time interval between the moving needles of said series of uniformly spaced needles, and wherein faulty needles will produce changes in the timing of such signals, whereby the presence of such faulty needles can be detected.

3. Apparatus as in claim 1 wherein said evaluating means includes a constantly charged capacitator, wherein the output signals of said amplifier causes said evaluating means to produce a pulse train of rectangularly shaped signals, and wherein said capacitor in response to said last named signals is caused to increase the level of its signal output when faulty needles are present, whereby the presence of such faulty needles can be detected.

* * * * *